United States Patent [19]

Gardiner

[11] Patent Number: 5,300,357
[45] Date of Patent: Apr. 5, 1994

[54] DURABLY HYDROPHILIC, THERMOPLASTIC FIBER AND FABRIC MADE FROM SAID FIBER

[75] Inventor: Robert A. Gardiner, Maplewood, Minn.

[73] Assignee: Minnesota Mining and Manufacturing Company, St. Paul, Minn.

[21] Appl. No.: 92,210

[22] Filed: Jul. 15, 1993

Related U.S. Application Data

[62] Division of Ser. No. 694,541, May 2, 1991, Pat. No. 5,244,951.

[51] Int. Cl.$^5$ ................................. D03D 3/00
[52] U.S. Cl. ........................... 428/224; 428/903; 428/913; 428/284
[58] Field of Search ............. 428/224, 903, 913, 284

[56] References Cited

U.S. PATENT DOCUMENTS

| | | | |
|---|---|---|---|
| 2,723,999 | 11/1955 | Cowen et al. | 260/615 |
| 2,915,554 | 12/1959 | Ahlbrecht et al. | 260/556 |
| 3,489,148 | 1/1970 | Duncan et al. | 128/284 |
| 3,592,194 | 7/1971 | Duncan | 128/287 |
| 3,787,351 | 1/1974 | Olson | 260/40 |
| 3,860,003 | 1/1975 | Buell | 128/287 |
| 3,870,567 | 3/1975 | Palmer et al. | 136/148 |
| 3,871,378 | 3/1975 | Duncan et al. | 128/290 |
| 3,899,563 | 8/1975 | Oxenrider et al. | 264/211 |
| 4,013,671 | 3/1977 | Gordon et al. | 260/42.55 |
| 4,093,775 | 6/1978 | Sumr | 428/394 |
| 4,104,452 | 8/1978 | Bernett | 260/561 |
| 4,215,205 | 7/1980 | Landucci | 525/331 |
| 4,324,246 | 4/1982 | Mullane et al. | 128/287 |
| 4,328,279 | 5/1982 | Meitner et al. | 428/289 |
| 4,426,466 | 1/1984 | Schwartz | 523/455 |
| 4,468,527 | 8/1984 | Patel | 564/96 |
| 4,540,497 | 9/1985 | Chang et al. | 252/8.8 |
| 4,566,981 | 1/1986 | Howells | 252/8.8 |
| 4,589,876 | 5/1986 | Van Tilburg | 604/385 |
| 4,855,360 | 8/1989 | Duchesne et al. | 525/187 |
| 4,857,251 | 8/1989 | Nohr et al. | 264/103 |
| 4,920,168 | 4/1990 | Nohr et al. | 524/188 |
| 4,933,229 | 6/1990 | Insley et al. | 428/224 |
| 5,043,195 | 8/1991 | Skrivseth | 428/35 |

FOREIGN PATENT DOCUMENTS

| | | |
|---|---|---|
| 0260011 | 6/1987 | European Pat. Off. |
| 77 2271309 | 3/1977 | France |
| 2-174002 | 7/1990 | Japan |

OTHER PUBLICATIONS

"Fluorocarbon Elastomer Aids Polyolefin Extrusion", Plastics Engineering, Mar. 1988, pp. 83–86.

Banks, R. E. "Organofluorine Chemicals and their Industrial Applications", (1979) pp. 226–234.

Mares, F. and Oxenrider, B. C. "Modification of Fiber Surfaces by Monomeric Additives, Part 1: Extrusion Techniques", Textile Research Journal vol. 47, pp. 551–561.

Wente, Boone, and Fluharty, Report No. 4364 of the Naval Research Laboratories "Manufacture of Superfine Organic Fibers".

Wente, Van A., "Superfine Thermoplastic Fibers" Industrial and Engineering Chemistry, vol. 48, p. 1342 (1956).

Primary Examiner—James J. Bell
Attorney, Agent, or Firm—Gary L. Griswold; Walter N. Kirn; Carole Truesdale

[57] ABSTRACT

Durably hydrophilic, thermoplastic fibers comprising thermoplastic polymer and fluoroaliphatic group-containing non-ionic compound are provided. Methods of preparation are also disclosed.

16 Claims, No Drawings

DURABLY HYDROPHILIC, THERMOPLASTIC FIBER AND FABRIC MADE FROM SAID FIBER

This is a division of application Ser. No. 07/694,541 filed May 2, 1991 is now U.S. Pat. No. 5,244,951.

This invention relates to fiber comprising thermoplastic polymer, such as polypropylene. In another aspect it relates to methods of preparation of durably hydrophilic fiber from normally hydrophobic thermoplastic polymer. In another aspect it relates to fabrics comprising durably hydrophilic fiber, useful, for example as liners for diapers, and methods of making such fabric.

Thermoplastic polymers are widely used to make variety of products, including for example, blown and cascade films, extruded sheets, foams, woven and knitted fabrics, and non-woven fibrous webs. Many thermoplastic polymers, such as polyolefins, are normally hydrophobic. There are a number of uses for thermoplastic polymers where their hydrophobic nature either limits their use or requires some effort to modify the surface of the shaped articles made therefrom. For example, polyolefins are used to manufacture nonwoven webs which are employed in the construction of absorbent articles such as diapers, feminine care products, and incontinence products, the use of such articles being limited due to their hydrophobic nature.

When fiber, and the fabric made therefrom, is still hydrophilic after contact with deionized water and drying, such fiber and fabric is said to have durable hydrophilicity. Hydrophilic fiber can be obtained by spraying or coating the fiber with surfactant followed by drying. Typically, the surfactant which remains on the fiber is diminished or completely lost upon contact with aqueous media, e.g. water, and thus the hydrophilicity of the fibers has poor durability. Hydrophilicity, or the lack thereof, can be measured in a variety of ways, for example, when water contacts a nonwoven web that has lost its hydrophilicity, the water does not flow through, or flows undesirably slow through, the web.

U.S. Pat. No. 4,328,279 (Meitner et al.) describes a wettable nonwoven wiper which is provided through the treatment of nonwoven material with a mixture of wetting agents. Mixtures of sodium dioctyl sulfosuccinate and a non-ionic surfactant, such as alkyl phenoxy ethanol, were used to treat nonwoven materials made from normally hydrophobic thermoplastic fibers. The nonwoven materials can be treated with the surfactant mixture by conventional techniques such as spraying, dipping, coating, impregnating, and printing.

U.S. Pat. No. 3,870,567 (Palmer et al.) describes a method for producing wettable nonwoven fibers from normally hydrophobic thermoplastic resins. These fibers are prepared from mixtures of thermoplastic resin, such as polypropylene, and internal wetting agent. It is very important to develop the wetting agent after the fiber has been cooled. Developing usually includes both heating and compression.

U.S. Pat. Nos. 4,857,251 (Nohr et al.) and 4,920,168 (Nohr et al.) describe a method of forming fibers by melt-extrusion of a surface segregatable thermoplastic composition which comprises thermoplastic polymer and siloxane-containing additive having certain moieties. After the fiber is formed, it is heated from 27° C. to 95° C. for a period of time sufficient to increase the amount of additive at the fiber surface. The resulting fiber has increased surface hydrophilicity compared to fibers prepared from the thermoplastic resin alone.

Fluoroalphatic groups are generally hydrophobic, and the use of various fluorochemical compositions on fibers or fibrous substrates, such as textiles, paper, and leather, to impart water repellency is known. See, for example, Banks, Ed., *Organofluorine Chemicals and Their Industrial Applications*, Elis Horwood Ltd., Chichester, England, 1979, pp 226–234. Such fluorochemical compositions include, for example, fluorochemical guanidines (U.S. Pat. No. 4,540,497, Chang), compositions of cationic and non-cationic fluorochemicals (U.S. Pat. No. 4,566,981, Howells), compositions containing fluorochemical carboxylic acid and epoxidic cationic resin (U.S. Pat. No. 4,426,466, Schwartz), fluoroaliphatic carbodiimides (U.S. Pat. No. 4,215,205, Landucci), and fluoroaliphatic alcohols (U.S. Pat. No. 4,468,527, Patel).

Fluorochemical compositions can be applied to various substrates by methods which include, for example, spraying, padding, and finish bath immersion. Textile fibers and yarns can also be treated by incorporation of the fluorochemical in fiber spin finishes and by melt extrusion of a blend of a synthetic fiber-forming polymer and a fluorochemical composition. Such melt extrusion is described, for example, by Mares, F. et al., "Modification of Fiber Surfaces by Monomeric Additives, Part I: Extrusion Techniques," *Textile Research Journal*, Vol. 48, No. 4, pp 218–229, and in U.S. Pat. No. 3,899,563 (Oxenrider et al.). Compounds may be incorporated into polymer melts by injection of the compound into the molten polymer stream immediately on exiting the extruder barrel according to the procedure described in U.S. Pat. No. 4,933,229 (Insley et al.).

European Pat. Pub. No. 0 260 011 (Crater et al.) discloses certain fluoroaliphatic group-containing oxazolidinone compositions. The Crater application also discloses fibers, films, and molded articles prepared, for example, by injection molding a blend or mixture of fiber-or film-forming synthetic organic polymers and certain fluorochemical oxazolidinones. The resulting fibers, films, and molded articles are said to have low surface energy, oil and water repellency, and anti-soiling properties.

U.S. Pat. No. 3,787,351 (Olson) discloses reinforced resin composite compositions wherein the wetting of the surface of particulate reinforcing material by resins is improved by the use of certain fluoroaliphatic radical-containing oligomers. Particular oligomers are copolymers of fluoroaliphatic radical-containing monomers and monomers with moieties that solubilize the resin. Useful solubilizing moieties include poly(oxyalkylene) moieties.

The use of certain fluorochemical compositions as processing aids in the extrusion of synthetic resins into fibers and films is also known. See for example, Rudkin et al., "Fluorocarbon Elastomer Aids Polyolefin Extrusion," *Plastics Engineering*, March 1986. pp 83–86 and U.S. Pat. No. 4,855,360 (Duchesne et al.).

U.S. Pat. No. 4,093,775 (Szur) discloses applying directly to a polymer shape, such as nylon films and filaments, or compouding with the polymeric material prior to shaping, or incorporating internally in the polymeric shape, non-ionic surfactants made from the reaction of 6-hydroxyhexyl perfluoroisopropylether or 2,2,3,4,4,4-hexafluorobutanol with ethylene oxide and/or propylene oxide. These non-ionic surfactants are said to be useful as antistatic agents, lubricants and antisoiling agents for polymeric shapes such as nylon films and filaments.

U.S. Pat. No. 5,043,195 (Gutman) describes flexible sheet material comprising an antistatic layer. Said antistatic layer comprises a polymer having dispersed therein a fluoroaliphatic sulfonamide polyether.

Briefly, the present invention, in one aspect, provides durably hydrophilic, thermoplastic fiber comprising a mixture of thermoplastic polymer, such as polyamide, polyurethane, or polyolefin, e.g. polypropylene, and fluoroaliphatic group-containing non-ionic compound which imparts durable hydrophilicity to the surface of the fiber. The compound is dispersed within the fiber and is present at the surface of the fiber. The compound is present in an amount sufficient to impart durable hydrophilicity to said surfaces. The fiber can be fabricated in the form of a durably hydrophilic nonwoven web.

The fluoroaliphatic group-containing non-ionic compounds useful in the present invention comprise a fluoroaliphatic group and a non-ionic water solubilizing group such as poly(oxyethylene), poly(oxypropylene), or poly(oxyethylene-co-oxypropylene). The fluoroaliphatic group contains sufficient fluorine so that the resulting fibers are durably hydrophilic. The fluoroaliphatic group-containing non-ionic compounds useful in the present invention are preferably those that result in durably hydrophilic fiber when the compounds are incorporated into the fiber at about 2% by weight or less, based on weight of the fiber. Larger amounts, e.g., up to 15% by weight can be used, but durable hydrophilicity does not substantially increase and the higher amounts may cause problems during extrusion.

Surprisingly, the compounds of this invention must contain at least four, and preferably at least 6, fully-fluorinated carbon atoms in the fluoroaliphatic group, in order to impart durable hydrophilicity to the fiber. Because fluoroaliphatic groups are hydrophobic, it is surprising that compounds with more fluorine impart hydrophilicity while compounds with less fluorine do not.

This invention also provides a method of preparation of durably hydrophilic fiber from a mixture or blend of thermoplastic film-forming polymer and fluoroaliphatic group-containing non-ionic compound. The melt of the mixture or blend is processed or shaped, for example, by extrusion or molding, to produce fibers with the compound dispersed within the fiber and present at the surfaces of the fiber, which surfaces are durably hydrophilic. Because non-ionic compounds demonstrate thermal sensitivity, it is preferred that processing temperatures in the extruder be kept below about 310° C., and more preferably below about 300° C. The durable hydrophilicity is achieved without requiring post fiber-spinning operations, for example heating, because the fiber is durably hydrophilic as extruded ("as made").

This invention also provides fabric, e.g. nonwoven web, comprising the durably hydrophilic fiber of this invention. The fabric of the present invention typically is more durably hydrophilic, including very good in-service durability, than fabric comprising comparable levels of fluorine-free compound.

The fabric of this invention can be prepared by post fiber-formation operations, such as weaving or knitting, or by direct processing, such as melt-blowing or spun-bond processes, of a melt of the thermoplastic polymer and compound mixture into a nonwoven fabric.

The durable hydrophilicity, or lack thereof, of fiber can be determined by subjecting a nonwoven web sample of such fiber to at least two cycles of the flow-rate hydrophilicity test described below. For brevity, the fiber is defined as having a "Hydrophilicity Index" equal to the number of cycles that a nonwoven web sample of such fiber can experience and still be hydrophilic as defined by the test. The higher the Hydrophilicity Index, the more durable is the hydrophilicity of the fiber. Fiber is hydrophilic if it has a Hydrophilicity Index of at least 1, and fiber is durably hydrophilic if it has a Hydrophilicity Index of at least 2. Hydrophilic fiber can be prepared from normally hydrophobic thermoplastic polymer resins which have a Hydrophilicity Index of zero.

This invention also provides aqueous media absorbent articles such as diapers, feminine care products, and adult incontinence products. Such articles comprise the fabric of this invention, which functions as the aqueous media absorbent structure in the articles. Such articles typically include an aqueous media impervious backing sheet, an aqueous media pervious top sheet, and an aqueous media absorbent core positioned between the backing sheet and the top sheet.

A class of fluoroaliphatic group-containing non-ionic compounds useful in the present invention can be represented by Formula I.

$$R_f\text{-}Q\text{-}Z \qquad\qquad I$$

In Formula I, $R_f$ is a fluoroaliphatic group, which is saturated, and mono-valent, and has at least 4 fully-fluorinated carbon atoms. It can be straight, branched, or, if sufficiently large, cyclic, or combinations thereof, such as alkylcycloaliphatic radicals. The skeletal chain in the fluoroaliphatic radical can include catenary oxygen, hexavalent sulfur, and/or trivalent nitrogen atoms bonded only to carbon atoms of the skeletal chain, such hetero atoms providing stable linkages between fluorocarbon portions of the $R_f$ radical. A fully fluorinated radical is preferred, but hydrogen or chlorine atoms may be present as substituents provided that not more than one atom of either is present for every two carbon atoms. While $R_f$ can contain a large number of carbon atoms, compounds where $R_f$ is not more than 20 carbon atoms will be adequate and preferred since larger radicals usually represent a less efficient utilization of the fluorine than is possible with shorter chains. Fluoroaliphatic radicals containing from about 6 to about 12 carbon atoms are most preferred. Generally $R_f$ will contain 40 to 78 weight percent fluorine. The terminal portion of the $R_f$ group preferably has at least four fully fluorinated carbon atoms, e.g., $CF_3CF_2CF_2CF_2-$, and the preferred compounds are those in which the $R_f$ group is fully or substantially completely fluorinated, as in the case where $R_f$ is perfluoroalkyl, e.g. $CF_3(CF_2)_n$-. Suitable $R_f$ groups include for example, $C_8F_{17}-$, $C_6F_{13}CH_2CH_2-$, and $C_{10}F_{21}-CH_2CH_2-$.

In the Formula, Q is a linking group, or a covalent bond, which provides a means to link $R_f$ with the depicted group Z, which is a non-ionic water-solubilizing group. The linking group, Q, can comprise a hetero atom-containing group, e.g., a group-containing $-S-$, $-O-$, and/or $-NR-$, or a combination of such groups, for example $-CO-$, $-CONR-$, $-SO_2-$, $-SO_2N(CH_3)-$, $-C_3H_6Cl-$, $-OC_2H_4-$, $-C_nH_{2n}-$ where n is 1 to 6.

The non-ionic water-solubilizing group Z comprises a poly(oxyalkylene) group, $(OR')_x$, where $R'$ is an alkylene group having 2 to 4 carbon atoms, such as $-CH_2CH_2-$, $-CH_2CH_2CH_2-$, $-CH(CH_3)CH_2-$, and $-CH(CH_3)CH(CH_3)-$, and x is from about 6 to about 20. The oxyalkylene units in said poly(oxyalkylene) being the same, as in poly(oxypropylene), or present as a mixture, such as in a heteric straight or branched chain of randomly distributed oxyethylene and oxypropylene units poly(oxyethylene-co-oxypropylene), or as in a straight or branched chain of blocks of oxyethylene units and blocks of oxypropylene units. The poly(oxyalkylene) chain can be interrupted by or include one or more catenary linkages, providing such linkages do not substantially alter the water-solubilizing character of the poly(oxyalkylene) chain. The Z group is terminated with hydroxyl or lower alkyl ether for example, $-OCH_3$ or $-OCH_2CH_3$. Examples of suitable Z groups include,

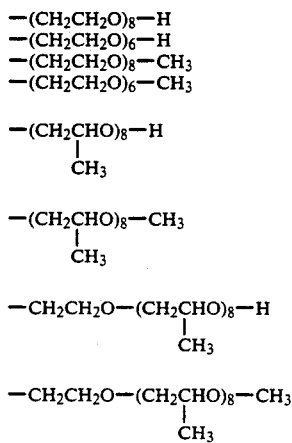

Compounds useful as fluoroaliphatic group-containing non-ionic compounds in the present invention can be prepared using known methods such as those described in U.S. Pat. No. 2,915,554 (Albrecht et al.) The Albrecht patent discloses the preparation of fluoroaliphatic group-containing non-ionic compounds from active hydrogen containing fluorochemical intermediates, such as fluoroaliphatic alcohols, e.g., $R_fC_2H_4OH$, acids, e.g., $R_fSO_2N(R')Ch_2CO_2H$, and sulfonamides, e.g., $R_fSO_2N(R')H$, by reaction of the intermediates with, for example, ethylene oxide to yield, respectively, $R_fC_2H_4O(C_2H_4O)_nH$, $R_fSO_2N(R')CH_2CO_2(C_2H_4O)_nH$, and $R_fSO_2N(R')(C_2H_4O)_nH$, where n is a number greater than about 3, and $R'$ is a hydrogen or lower alkyl (e.g., 1 to 6 carbons). Analogous compounds can be prepared by treating the intermediates with propylene oxide or a mixture of ethylene oxide and propylene oxide. See also the fluoroaliphatic oligomers disclosed in U.S. Pat. No. 3,787,351 (Olson), and certain fluorinated alcohol-ethylene oxide condensates described in U.S. Pat. No. 2,723,999 (Cowen et al.), which descriptions are hereby incorporated by reference.

"fiber" and "fibrous" referes to particulate material wherein the length to diameter ratio of such particulate material is greater than about 10. The term "fiber" includes fiber sizes ranging from about 0.5 micron diameters to diameters in excess of 1.0 millimeter. The term includes textile materials in the form of a mass, aggregation, or collection of fibers, continuous fibers of indeterminant length, spun yarns, filaments, rovings, slivers, tows and the like. Fiber may have a variety of cross-sectional geometries, and may be solid or hollow. Fiber may optionally be colored by, e.g., incorporating soluble dye in the polymer melt.

The fiber of this invention, in addition to having modifed surface characteristics, also contains said fluoroaliphatic compound within the fiber. The compound within the fiber is believed to act as a reservoir of internal wetting agent to resupply the surface upon removal of the compound already present on the surface. When the fiber and fabric of this invention are exposed to water, they retain their hydrophilic nature after repeated exposures to deionized water. This durable hydrophilicity is obtained at much lower levels than with fluorine-free compounds within the fiber. Thus the fiber of the present invention is durably hydrophilic. The fluoroaliphatic group-containing compound contained within the fiber is distributed or dispersed within the fiber such that there is no visible difference, as viewed with a microscope, between fiber containing the compound and fiber without the compound.

The fabrics of this invention possess much greater surface area per weight then would films of the thermoplastic polymer and non-ionic compound and thus are useful for absorption applications. The fabrics are also better than the films would be in removing liquid from the skin surface.

The fabrics of the present invention are readily prepared by processes used in the manufacture of meltblown or spun-bonded webs. For example, a process similar to that described in Wente, "Superfine Thermoplastic Fibers," in Industrial Engineering Chemistry, Vol. 48, pages 1342 et seq. (1956), or in Report No. 4364 of the Naval Research Laboratories, published May 25, 1954, entitled "Manufacture of Superfine Organic Fibers" by Wente, Boone, and Fluharty, can be used for the preparation of the fabrics of the present invention.

Thermoplastic polymers useful in the present invention are generally normally hydrophobic polymers and include fiber-forming polyolefins such as polyethylene, polypropylene, polybutylene, and blends. Other useful fiber-forming thermoplastic polymers include thermoplastic polyesters, polyurethanes and polyamides.

The amount of fluoroaliphatic group-containing non-ionic compound incorporated in the thermoplastic polymer can vary. The amount to be used will be that amount sufficient to improve the wetting of the surface of the resulting fiber. Compounds that are effective at lower levels are more economical and are easier to process. The fluoroaliphatic compounds useful in this invention are preferably those that are effective when incorporated within the thermoplastic polymer at up to 2 weight percent and more preferably at up to 1 weight percent.

Levels of compound higher than 2 weight percent may cause extruder stability problems. Therefore, when fabrics containing greater than 2 weight percent compound or surfactant are prepared, it is preferable to inject the compound into the molten polymer stream under high pressure either in the extruder barrel or immediately as the melt stream exits the extruder and before it enters the extrusion die. High pressure injection can be accomplished by using a high pressure metering pump, such as those available from Ruska or Zenith, to pump liquid compound into the molten polymer in the metering or transition zone of the extruder. Alternatively, high pressure injection can be accomplished by means of a cascade extrusion apparatus wherein liquid compound is introduced into the barrel of a first extruder at the metering section of the screw by means of a Ruska or Zenith pump and the effluent compound stream is subsequently injected into the second extruder at the metering section of the screw. High pressure injection may also be accomplished by injection of the compound into the molten polymer stream immediately on exiting the extruder barrel according to the procedure described in U.S. Pat. No. 4,933,229 (Insley et.al.), which description is incorporated herein by reference. When fabrics containing less than about 2 weight percent compound are prepared, the compound is conveniently incorporated into the polymer by tumble blending the compound with resin pellets prior to extrusion or by metering liquid compound into the extruder hopper along with the resin pellets during extrusion.

Additionally, fiber of this invention typically can contain at least from two to five times less compound, to develop hydrophilicity of comparable durability, than fibers containing fluorine-free compound. The lower compound levels provide for improved extruder stability and subsequent fiber uniformity as extruder screw slippage problems are significantly reduced.

The durability of the hydrophilicity of the fiber of the present invention is particularly surprising in view of the significant increase in surface area (i.e., polymer/air interface) relative to films containing comparable levels of surfactant. For example, if a gram of polypropylene resin is converted into fiber having an average diameter of 10 microns, and into a 0.025 mm thick film, the fiber will have approximately five times the surface area of the film. If the hydrophilicity is indeed produced simply by the migration of the compound to the surface of the fiber, one would reasonably except a higher surface area would lead to a more rapid depletion of the compound within the fiber and thus, to a less durable hydrophilic treatment.

The fiber and fabrics of this invention can be used to prepare aqueous media absorbent articles such as diapers, feminine care products, and adult incontinence products, which utilize the fabrics of the present invention as at least a portion of their fluid-absorbing "core" element. By "absorbent article" herein is meant a consumer product which is capable of absorbing significant quantities of water and other aqueous fluids (i.e. liquids), like body fluids. Examples of aqueous media absorbent articles include disposable diapers, sanitary napkins, tampons, incontinence pads, disposable training pants, paper towels, facial tissues, and the like. The fabrics of the present invention are particularly suitable for use in articles like sanitary napkins, diapers and incontinence pads.

Aqueous media absorbent articles will frequently comprise a substantially aqueous media impervious backing sheet, an aqueous media pervious top sheet and an aqueous media absorbent core comprising an aqueous media absorbent structure positioned between said backing sheet and said top sheet. Said impervious backing sheets can comprise any material, for example polyethylene or polypropylene having a thickness of about 0.038 mm, which will help retain fluid within the absorbent article. Said pervious top sheets can comprise any material such as polyester, polyolefin, rayon and the like which is substantially porous and permits aqueous media to readily pass therethrough into the underlying absorbent core. Suitable materials for top sheets and bottom sheets are well known in the art.

A more detailed description of sanitary napkins and suitable materials for use therein is found in U.S. Pat. Nos. 3,871,378 (Duncan et al.), 4,324,246 (Smith et al.), and 4,589,876 (Van Tillberg), which are incorporated herein by reference.

Disposable diapers comprising the hydrophilic fabrics of the present invention may be made by using conventional diaper making techniques, but by replacing or supplementing the wood pulp fiber web core which is typically used in conventional diapers with the hydrophilic fabrics of the present invention. The hydrophilic fabrics of this invention may thus be used in diapers in single layer or various multiple layer core configurations. Articles in the form of disposable diapers are described in U.S. Pat. Nos. 3,592,194 (Duncan et al.), 3,489,148 (Duncan et al.), and 3,860,003 (Buell), which are incorporated herein by reference.

Objects and advantages of this invention are illustrated in the Examples below.

EXAMPLES

Mixtures of fluoroaliphatic group-containing non-ionic compounds and thermoplastic polymers were prepared. Blown microfiber webs were prepared from fiber of these mixtures. The durability of the hydrophilicity of the fiber was determined by evaluation of the webs made therefrom, and compared to webs prepared from mixtures containing fluorine-free non-ionic surfactants and webs prepared from thermoplastic polymer alone.

Thermoplastic Polymers

Polymer A

PP3505, a 400 melt flow index polypropylene resin available from Exxon Corp.

Polymer B

PP3435, a 70 melt flow index polypropylene resin available from Exxon Corp.

Polymer C 3860X, a 50 melt flow index polypropylene resin available from Fina Chemicals.

Polymer D

PP3085, a 35 melt flow index polypropylene resin available from Exxon Corp.

Polymer E

PF442, an 800 melt flow index polypropylene resin available from Himont.

Polymer F

PP3495, an 800 melt flow index polypropylene resin available from Exxon Corp.

Polymer G

PS455, a 32 melt flow index poly(ester/urethane) available from Morton Thiokol Corp., Malden, Mass.

Polymer H

BASF B3F, a 120 melt flow index Nylon 6 resin available from BASF.

Polymer I

PE6814, a 125 melt flow index polyethylene available from Dow Corp.

Polymer J

PB0400, a 20 melt flow polybutylene available from Shell.

Polymer K

PS440, a polyester-urethane available from Morton Thiokol Corp.

Fluoroaliphatic Group-Containing Non-Ionic Compounds

Compound I

Fluoroaliphatic group-containing non-ionic compound of structure

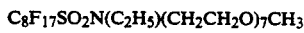
$C_8F_{17}SO_2N(C_2H_5)(CH_2CH_2O)_7CH_3$ was prepared according to U.S. Pat. No. 2,915,554 (Ahlbrecht et. al.).

Compound II

Fluoroaliphatic group-containing non-ionic compound of structure

$C_8F_{17}SO_2N(C_2H_5)CH_2CH_2O(CH_2CH(CH_3)O)_8H$ was prepared according to U.S. Pat. No. 2,915,554 (Ahlbrecht et. al.).

Fluorine-Free Non-Ionic Surfactants

Comparative fluorine-free non-ionic surfactants which were evaluated include:

CA—TRITON ™ X-100, a poly(ethylene oxide) based surfactant available from Rohm and Haas Corp.

CB—EMEREST ™ 2620, a polyethylene glycol monolaurate based surfactant available from Emery Industries.

CC—SILWET ™ L-77, a polyalkylene oxide modified polydimethylsiloxane based surfactant available from Union Carbide.

CD—SILWET ™ L-720, a polyalkylene oxide modified polydimethylsiloxane based surfactant available from Union Carbide.

CE—SILWET ™ L-7600, a polyalkylene oxide modified polydimethylsiloxane based surfactant available from Union Carbide.

CF—SILWET ™ L-7602, a polyalkylene oxide modified polydimethylsiloxane based surfactant available from Union Carbide.

Mixing Methods

The above compounds or surfactants, and polymers were mixed as described below. Because non-ionic compounds and surfactants demonstrate thermal sensitivity it is preferred that processing temperatures in the extruder be kept below about 310° C., and more preferably below about 300° C.

Tumble Blending (TB)

Compound or surfactant, and thermoplastic polymer mixtures were prepared by tumble blending the compound or surfactant, and the polymer in a plastic bag for about five minutes until a homogeneous mixture was obtained.

Barrel Injection (BI)

Compound or surfactant, and thermoplastic polymer mixtures were prepared by pumping the compound or surfactant into the metering section of the extruder by means of a ZENITH ™ pump. Compound or surfactant incorporation levels were controlled by adjusting the pump rpm rate.

Cascade Extrusion (CE)

Compound or surfactant, and thermoplastic polymer mixtures were prepared by pumping the compound or surfactant into the metering section of a extruder by means of a ZENITH ™ pump. The effluent stream from this extruder was then fed into the metering section of a second extruder where the compound or surfactant was mixed with the molten polymer. Compound or surfactant incorporation levels were controlled by adjusting the rpm rate of the first extruder.

Preparation of Blown Microfiber Webs

A melt-blowing process is described, for example, in Wente, Van A., "Superfine Thermoplastic Fibers," in Industrial Engineering Chemistry, Vol. 48, pages 1342 et seq (1956), and in Report No. 4364 of the Naval Research Laboratories, published May 25, 1954, entitled "Manufacture of Superfine Organic Fibers" by Wente, Boone, and Fluharty. This process was used to prepare blown microfiber webs, except that the melt blowing die had circular smooth surfaced orifices (10/cm) with a 5:1 length to diameter ratio. Extrusion was carried out at the temperature indicated in Tables 1–3, the primary air temperature was maintained at approximately the temperature indicated in Tables 1–3, at a pressure of 124 kPa (18 psi) (0.076 cm air gap width), and the polymer throughput rate was about 180 gm/hr/cm. The resulting average diameter of the small diameter fibers was about 5–18 micrometers and the basis weight of the blown microfiber webs was 55±5 g/m². In the instances where the Barrel Injection or Cascade Extrusion processes were used to incorporate the compound or surfactant into the resin, the melt blowing apparatus was modified by the addition of a ZENITH ™ high pressure metering pump or a second extruder respectively, which fed into the metering zone of the extruder connected to the die.

Examples 1–28

Fluoroaliphatic group-containing non-ionic compound loaded blown microfiber webs were prepared utilizing the above thermoplastic polymers and fluoroaliphatic group-containing non-ionic compounds. Experimental conditions along with the mixing method used to incorporate the fluoroaliphatic group-containing non-ionic compound into the blown microfiber web are shown in Table 1.

TABLE 1

Fluoroaliphatic Group-Containing Non-Ionic Compound Loaded Webs

| Example | Thermoplastic Polymer | Fluoroaliphatic Non-Ionic Compound | Compound Level (w/w %) | Mixing Method | Extrusion Temp. (°C.) | Primary Air Temp. (°C.) |
|---------|-----------------------|------------------------------------|------------------------|---------------|-----------------------|-------------------------|
| 1 | A | I | 0.4 | TB | 200 | 210 |
| 2 | A | I | 0.5 | TB | 200 | 210 |
| 3 | A | I | 0.75 | TB | 200 | 210 |
| 4 | A | I | 1.0 | TB | 200 | 210 |
| 5 | A | I | 2.0 | BI | 200 | 210 |
| 6 | A | I | 4.0 | CE | 200 | 210 |
| 7 | A | I | 5.0 | CE | 200 | 210 |
| 8 | A | I | 11.4 | CE | 200 | 210 |

TABLE 1-continued

| | | Fluoroaliphatic Group-Containing Non-Ionic Compound Loaded Webs | | | | |
|---|---|---|---|---|---|---|
| Example | Thermoplastic Polymer | Fluoroaliphatic Non-Ionic Compound | Compound Level (w/w %) | Mixing Method | Extrusion Temp. (°C.) | Primary Air Temp. (°C.) |
| 9 | B | I | 1.0 | TB | 240 | 255 |
| 10 | B | I | 1.0 | TB | 250 | 253 |
| 11 | B | I | 1.0 | TB | 260 | 253 |
| 12 | B | I | 1.0 | TB | 270 | 273 |
| 13 | B | I | 1.0 | TB | 280 | 280 |
| 14 | B | I | 1.0 | TB | 290 | 285 |
| 15 | B | I | 1.0 | TB | 300 | 292 |
| 16 | C | I | 1.0 | TB | 285 | 289 |
| 17 | D | I | 1.0 | TB | 290 | 295 |
| 18 | E | I | 1.0 | TB | 230 | 243 |
| 19 | F | I | 1.0 | TB | 230 | 242 |
| 20 | A | I | 1.0 | TB | 260 | 266 |
| 21 | G | I | 1.0 | TB | 210 | 210 |
| 22 | H | I | 1.0 | TB | 280 | 280 |
| 23 | H | II | 1.0 | TB | 280 | 290 |
| 24 | I | I | 1.0 | TB | 200 | 204 |
| 25 | I | II | 1.0 | TB | 200 | 204 |
| 26 | J | I | 1.0 | TB | 310 | 310 |
| 27 | J | II | 1.0 | TB | 310 | 310 |
| 28 | K | I | 1.0 | TB | 230 | 230 |

Comparative Examples C1–C14

Comparative blown microfiber webs were prepared, utilizing commercially available hydrocarbon non-ionic surfactants in place of the fluoroaliphatic group-containing compounds, according to the procedure described above. All used thermoplastic polymer A. The type and loading level of the surfactant, the extrusion temperature, the mixing method, and the primary air temperature were varied as shown in Table 2.

TABLE 2

| | Fluorine-Free Non-Ionic Surfactant Loaded Comparative Webs | | | | |
|---|---|---|---|---|---|
| Primary Comparative Example | Surfactant | Surfactant Level (w/w %) | Mixing Method | Extrusion Temp. (°C.) | Air Temp. (°C.) |
| C1 | CA | 1.0 | TB | 200 | 210 |
| C2 | CA | 2.0 | TB | 200 | 210 |
| C3 | CA | 4.0 | CE | 200 | 210 |
| C4 | CA | 4.5 | CE | 200 | 225 |
| C5 | CA | 5.0 | CE | 200 | 225 |
| C6 | CA | 7.7 | CE | 200 | 225 |
| C7 | CA | 11.8 | CE | 200 | 225 |
| C8 | CA | 13.6 | CE | 200 | 209 |
| C9 | CB | 5.0 | TB | 200 | 254 |
| C10 | CB | 6.4 | CE | 200 | 209 |
| C11 | CC | 1.0 | TB | 270 | 268 |
| C12 | CD | 1.0 | TB | 270 | 273 |
| C13 | CE | 1.0 | TB | 270 | 273 |
| C14 | CF | 1.0 | TB | 270 | 273 |

Comparative Examples C15–C20

Comparative blown microfiber webs were prepared according to the above described procedure, utilizing thermoplastic polymer alone with no compound or surfactant. The thermoplastic polymer used, the extrusion temperature and the primary air temperature were varied as shown in Table 3.

TABLE 3

| Comparative Webs Without Compound or Surfactant | | | |
|---|---|---|---|
| Comparative Example | Polymer | Extrusion Temp.(°C.) | Primary Air Temp. (°C.) |
| C15 | B | 280 | 278 |
| C16 | C | 285 | 285 |

TABLE 3-continued

| Comparative Webs Without Compound or Surfactant | | | |
|---|---|---|---|
| Comparative Example | Polymer | Extrusion Temp.(°C.) | Primary Air Temp. (°C.) |
| C17 | D | 310 | 305 |
| C18 | E | 230 | 243 |
| C19 | F | 230 | 241 |
| C20 | A | 260 | 266 |

Comparative Example C21

Comparative Example C21 was prepared with the identical ingredients and procedure as in Example 15 except that the extrusion temperature was 310° C. instead of 300° C. and the primary air temperature was 288° C. instead of 292° C.

Hydrophilicity Index

The durability of the hydrophilicity of the fiber used to prepare the above webs was determined by monitoring the time required for 200 mL of deionized water (D. I. water) to flow through a sample of the web mounted in a test fixture ("flow-rate test"). The test fixture consisted of two pipe cylinders, each cylinder having a diameter of 10 cm and a height of 12.5 cm. The two cylinders were abutted together with a sample of the web separating the two sections leaving an area of approximately 66 cm² of the web exposed for the flow test. The test fixture was mounted in a vertical configuration and 200 mL of D. I. water was poured into the upper cylinder along the inner side of the upper pipe cylinder onto the web so as to avoid a forceful impingement of the D. I. water on the web sample.

The prepared web sample thicknesses were from 0.036 mm to 0.61 mm as determined by using an ONO SOKKI ™ Model EG-225 Digital Linear Gauge equipped with a measuring foot diameter of 34.3 mm. Triplicate samples were cut from the substrate to be measured. The digital gauge was zeroed, a sample was centered on the platform under the measuring foot and the measuring foot was lowered on to the sample with a force of 150 g. The reading was allowed to stabilize for about 1 minute and the displayed value was recorded. The instrument was rezeroed and the procedure repeated for each sample. The value reported was the average of the three readings.

Flow-rate test data was reported as the time required (in seconds) for all of the D. I. water (200 ml) to flow through the web. A flow rate of greater then 300 seconds is defined as a failure of that cycle and interpreted to mean that the sample is no longer hydrophilic. Subsequent to each test cycle, the web sample was removed from the test fixture, allowed to dry for 24 hrs, and the test procedure repeated. Web samples were subjected to six repeats, or cycles, of the flow test, or until the sample failed a cycle. The results are summarized in Table 4 and 5.

Data was recorded as the number of seconds required for the D. I. water to completely flow through the sample. Samples for which D. I. water did not even begin to flow through were recorded as nonwetting (NW). The test was stopped after 300 seconds; samples where D. I. water was flowing through were recorded as >300. Samples that were nonwetting were not subjected to further cycles.

The results are interpreted to mean that flow of water through the sample in less then 300 seconds indicates hydrophilicity. Samples which do not allow water to flow through in 300 seconds of contact are interpreted to no longer be hydrophilic. Durability of hydrophilicity is the retention of hydrophilicity after at least one cycle. The longer (more cycles) that hydrophilicity is retained, the more durable is that sample's hydrophilicity. For brevity, the fiber is defined as having "Hydrophilicity Index" equal to the number of cycles that a nonwoven web sample of such fiber can experience and still be hydrophilic. Hydrophilicity Index equals the number of cycles of the flow-rate test that the sample experiences without a failure. The higher the Hydrophilicity Index, the more durable is the hydrophilicity of the fiber. Fiber is hydrophilic if it has a Hydrophilicity Index of at least 1, and fiber is durably hydrophilic if it has a Hydrophilicity Index of at least 2.

TABLE 4

| Example | Initial | after Cycle 1 | after Cycle 2 | after Cycle 3 | after Cycle 4 | after Cycle 5 | after Cycle 6 |
|---|---|---|---|---|---|---|---|
| 1 | 8 | 8 | 33 | 100 | 300 | >300 | >300 |
| 2 | 5 | 12 | 68 | 160 | 200 | 200 | 270 |
| 3 | 5 | 8 | 21 | 48 | 130 | 182 | 187 |
| 4 | 4 | 6 | 10 | 27 | 45 | 97 | 99 |
| 5 | 2 | 2 | 2 | 2 | 2 | 2 | 2 |
| 6 | 2 | 2 | 2 | 2 | 2 | 2 | 2 |
| 7 | 1 | 1 | 1 | 1 | 1 | 1 | 1 |
| 8 | 1 | 1 | 1 | 1 | 1 | 1 | 1 |
| 9 | 1 | 4 | 20 | 138 | NW | — | — |
| 10 | 1 | 4 | 20 | 87 | 300 | 300 | 300 |
| 11 | 2 | 3 | 26 | 49 | 300 | 300 | NW |
| 12 | 4 | 6 | 31 | 98 | 300 | 300 | 300 |
| 13 | 4 | 6 | 14 | 186 | 300 | 300 | 300 |
| 14 | 7 | 10 | 12 | 300 | 300 | 300 | 300 |
| 15 | 13 | 14 | 32 | 300 | NW | — | — |
| 16 | 10 | 10 | 12 | 57 | 300 | — | — |
| 17 | 8 | 8 | 26 | 89 | 300 | — | — |
| 18 | 6 | 9 | 52 | 300 | 300 | 300 | — |
| 19 | 6 | 8 | 21 | 61 | 300 | 300 | — |
| 20 | 5 | 9 | 15 | 37 | 57 | 57 | 39 |
| 21 | 10 | 10 | 12 | 17 | 18 | 20 | 20 |
| 22 | 7 | 8 | 8 | 9 | 11 | 15 | 16 |
| 23 | 3 | 4 | 4 | 6 | 6 | 8 | 84 |
| 24 | 3 | 3 | 3 | 3 | 3 | 3 | 3 |
| 25 | 3 | 3 | 3 | 3 | 3 | 3 | 3 |
| 26 | 20 | 55 | 69 | 124 | >300 | >300 | >300 |
| 27 | 51 | 59 | 68 | 72 | 88 | 102 | 108 |
| 28 | 6 | 6 | 6 | 7 | 13 | 15 | 18 |

TABLE 5

| Comparative Example | initial | after Cycle 1 | after Cycle 2 | after Cycle 3 | after Cycle 4 | after Cycle 5 | after Cycle 6 |
|---|---|---|---|---|---|---|---|
| C1 | NW | — | — | — | — | — | — |
| C2 | NW | — | — | — | — | — | — |
| C3 | 24 | 12 | 71 | >300 | NW | — | — |
| C4 | 2 | 3 | 5 | 9 | 14 | 42 | 105 |
| C5 | 3 | 3 | 3 | 36 | 161 | >300 | >300 |
| C6 | 2 | 3 | 3 | 4 | 4 | 10 | 22 |
| C7 | 2 | 2 | 2 | 3 | 3 | 3 | 4 |
| C8 | 1 | 2 | 2 | 2 | 2 | 2 | 3 |
| C9 | 25 | 155 | 191 | 205 | 300 | 300 | 300 |
| C10 | 2 | 2 | 2 | 2 | 2 | 2 | 2 |
| C11 | NW | — | — | — | — | — | — |
| C12 | NW | — | — | — | — | — | — |
| C13 | NW | — | — | — | — | — | — |
| C14 | NW | — | — | — | — | — | — |
| C15 | NW | — | — | — | — | — | — |
| C16 | NW | — | — | — | — | — | — |
| C17 | NW | — | — | — | — | — | — |
| C18 | NW | — | — | — | — | — | — |
| C19 | NW | — | — | — | — | — | — |
| C20 | NW | — | — | — | — | — | — |
| C21 | NW | — | — | — | — | — | — |

Table 6 summarizes the hydrophilicity, after six cycles, of the fabrics of this invention compared to fabrics comprising hydrocarbon non-ionic surfactants. Each of the samples in Table 6 utilized thermoplastic polymer A. Hydrophilicity is summarized as; "none" where samples required 300 seconds or more, "fair" where samples required 100 seconds or more, and "excellent" where samples required less than 100 seconds. All hydrophilicity data in Table 6 is a summary of the data, in Tables 4 and 5, for hydrophilicity after 6 cycles.

TABLE 6

Comparison of Durability

| Example | Surfactant | Surfactant Level (w %) | Hydrophilicity After 6 Cycles |
|---|---|---|---|
| 1 | I | 0.4 | none |
| 2 | I | 0.5 | fair |
| 3 | I | 0.75 | fair |
| 4 | I | 1 | excellent |
| 5 | I | 2 | excellent |
| 6 | I | 4 | exellent |
| 7 | I | 5 | excellent |
| 8 | I | 11.4 | excellent |
| Comparative Example | | | |
| C1 | CA | 1 | none |
| C2 | CA | 2 | none |
| C3 | CA | 4 | none |
| C4 | CA | 4.5 | fair |
| C5 | CA | 5 | none |
| C6 | CA | 7.7 | excellent |
| C7 | CA | 11.8 | excellent |
| C8 | CA | 13.6 | excellent |
| C9 | CB | 5 | none |
| C10 | CB | 6.4 | excellent |
| C11 | CC | 1 | none |
| C12 | CD | 1 | none |
| C13 | CE | 1 | none |
| C14 | CF | 1 | none |
| C20 | none | 0.0 | none |

Table 6 shows that fibrous webs loaded with fluoroaliphatic group-containing non-ionic compounds of this invention are more hydrophilic than webs loaded with comparable levels of fluorine-free non-ionic surfactants. Durable hydrophilicity is achieved with fluoroaliphatic group-containing non-ionic compounds at lower concentrations than with fluorine-free surfactants. Fibers containing fluoroaliphatic group-containing non-ionic compounds have a Hydrophilicity Index of 6 when they are present in the fiber at levels of about 1 weight percent. That is they give fibrous webs that are still hydrophilic after six cycles at levels of about 1 weight percent, while the comparative examples do not achieve a Hydrophilicity Index of 6 until surfactant levels are at least 4.5 weight percent.

The various modifications and alterations of this invention will be apparent to those skilled in the art without departing from the scope and spirit of this invention and this invention should not be restricted to that set forth herein for illustrative purposes.

I claim:

1. A fabric comprising durably hydrophilic, thermoplastic fiber comprising thermoplastic polymer and fluoroaliphatic group-containing non-ionic compound dispersed within said fiber and present at the surface of the fiber.

2. The fabric of claim 1 wherein said thermoplastic polymer is processable at a temperature below 310° C., and wherein said compound is thermally stable at said temperature.

3. The fabric of claim 1 wherein said thermoplastic polymer is normally hydrophobic and is selected from the group consisting of polyolefin, polyamide, polyester, polyurethane, and blends thereof.

4. The fabric of claim 1 wherein said fluoroaliphatic group-containing non-ionic compound is present in an amount sufficient to impart durable hydrophilicity to said surface.

5. The fabric of claim 4 wherein said fluoroaliphatic group-containing non-ionic compound is present in up to 2 weight percent based on weight of polymer.

6. The fabric of claim 4 wherein said fiber has a Hydrophilicity Index of at least 2.

7. The fabric of claim 1 wherein said fluoroaliphatic group-containing non-ionic compound is represented by the formula $$R_f\text{-}Q\text{-}Z$$

where $R_f$ is a saturated, mono-valent, fluoroaliphatic group comprising an alkyl group of at least 4 fully-fluorinated carbon atoms;
Q is a linking group; and
Z is a non-ionic water-solubilizing group.

8. The fabric of claim 7 wherein said water-solubilizing group comprises poly(oxyalkylene).

9. The fabric of claim 8 wherein said poly(oxyalkylene) is selected from the group consisting of poly(oxyethylene), poly(oxypropylene), and poly(oxyethylene-co-oxypropylene).

10. The fabric of claim 7 wherein said Q is $-SO_2N(-R)-$, where R is an alkyl group of 1 to 4 carbon atoms.

11. The fabric of claim 10 wherein said polymer is polypropylene, said $R_f$ is $C_8F_{17}$-, and said Z is selected from the group consisting of $-(CH_2CH_2O)_nR$, and $-CH_2CH_2O(CH_2CH(CH_3)O)_nR$, where n is from 6 to 9, and where R is H or $CH_3$.

12. The fabric of claim 1, wherein the fiber thereof is durably hydrophilic as made.

13. The fabric of claim 1 wherein said fabric comprises a nonwoven web.

14. The hydrophilic fabric of claim 13 wherein said nonwoven web comprises a melt blown web.

15. The fabric of claim 14 wherein said melt blown web comprises a blown microfiber web.

16. A multi-layer, aqueous liquid absorbent, article comprising:
 a) an aqueous liquid impervious backing sheet;
 b) a aqueous liquid pervious topsheet; and
 c) an aqueous liquid absorbent layer positioned between said backing sheet and said topsheet, said absorbent layer comprising a web of durably hydrophilic, thermoplastic polymer and fluoroaliphatic group-containing non-ionic compound dispersed within said fiber and present at the surface of the fiber.

* * * * *

UNITED STATES PATENT AND TRADEMARK OFFICE
CERTIFICATE OF CORRECTION

PATENT NO. : 5,300,357
DATED : April 5, 1994
INVENTOR(S) : Robert A. Gardiner

It is certified that error appears in the above-indentified patent and that said Letters Patent is hereby corrected as shown below:

| | |
|---|---|
| Col. 1, line 16 | "cascade" should read -- cast -- |
| Col. 5, line 47 | "$R_fSO_2N(R')Ch_2CO_2H$," should read -- $R_fSO_2N(R')CH_2CO_2H$, -- |
| Col. 5, line 61 | ""fiber"" should read -- "Fiber" -- |
| Col. 7, line 36 | "except" should read -- expect -- |
| Col. 14, Table 4 | delete "4" and insert in its place -- 3 --; and |
| Example 10 across: | delete "20" and insert in its place -- 24 --. |
| Col. 16, line 55 | between "thermoplastic" and "polymer" insert -- fiber, said fiber comprising thermoplastic -- |

Signed and Sealed this

Fourth Day of October, 1994

Attest:

BRUCE LEHMAN

*Attesting Officer*   *Commissioner of Patents and Trademarks*